United States Patent [19]

Lum et al.

[11] Patent Number: 5,507,294
[45] Date of Patent: Apr. 16, 1996

[54] ULTRASOUND DIAGNOSTIC PROBE HAVING NON-ROTATING ACOUSTIC IMAGING WAVEGUIDE

[75] Inventors: Paul Lum; Michael Greenstein, both of Los Altos; Edward Verdonk, Redwood City, all of Calif.

[73] Assignee: Hewlett Packard Company, Palo Alto, Calif.

[21] Appl. No.: 373,676

[22] Filed: Jan. 17, 1995

[51] Int. Cl.$^6$ ........................................................ A61B 8/12
[52] U.S. Cl. ................................................... 128/662.060
[58] Field of Search ...................... 128/662.06, 663.010, 128/660.090, 660.100

[56] References Cited

U.S. PATENT DOCUMENTS

| | | | |
|---|---|---|---|
| 4,794,931 | 1/1989 | Yock | 128/660.030 |
| 5,000,185 | 3/1991 | Yock | 128/662.030 |
| 5,029,588 | 7/1991 | Yock et al. | 128/660.030 |
| 5,059,851 | 10/1991 | Corl et al. | 128/657 X |
| 5,152,291 | 10/1992 | Dias | 128/662.060 |
| 5,176,141 | 1/1993 | Bom et al. | 128/662.060 |
| 5,240,003 | 8/1993 | Lancee et al. | 128/662.060 |
| 5,271,402 | 12/1993 | Yeung et al. | 128/660.100 |
| 5,284,148 | 2/1994 | Dias et al. | 128/662.060 |
| 5,371,483 | 12/1994 | Bhardwaj | 128/662.060 X |
| 5,400,788 | 3/1995 | Dias et al. | 128/662.060 X |

Primary Examiner—Francis Jaworski

[57] ABSTRACT

A catheter apparatus for obtaining an image of interior surface characteristics of a vascular vessel is provided. The catheter apparatus comprises an outer tubular element adapted for insertion into the vascular vessel, a rotatable inner tubular element disposed within the outer tubular element, and a non-rotating acoustic waveguide disposed within the inner tubular element and coupled to a source of an ultrasonic signal located external to the vascular vessel. The inner tubular element is rotated about an axis of the vascular vessel by use of an external driving member, such as a motor. The inner tubular element is provided with an acoustic reflecting or refracting element that directs the ultrasonic signal from a distal end of the acoustic waveguide through the outer tubular element at an angle relative to the axis of the vascular vessel. Sterile fluid disposed between the outer and inner tubular elements provides for acoustic coupling of the ultrasonic signal into the vessel, and further provides for lubrication of the rotating elements.

20 Claims, 3 Drawing Sheets

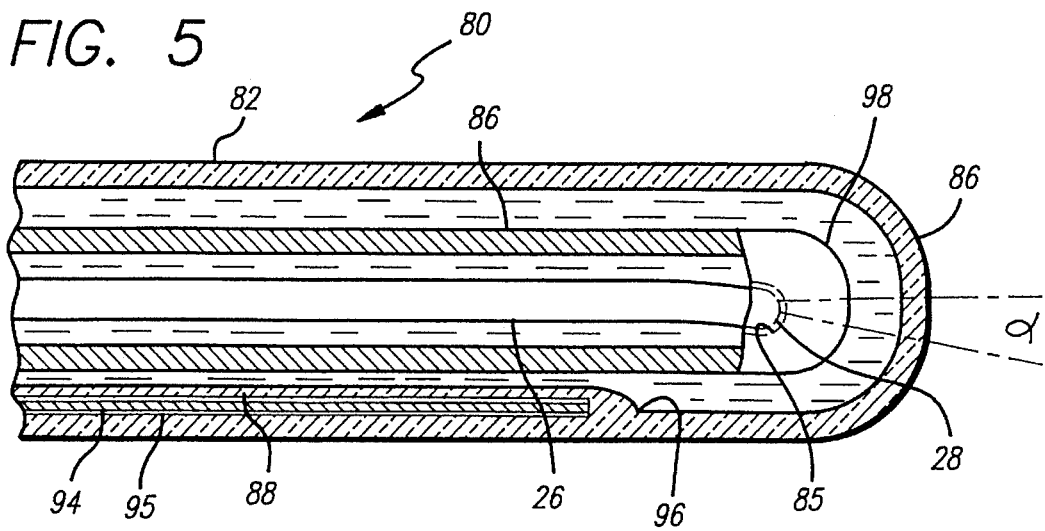
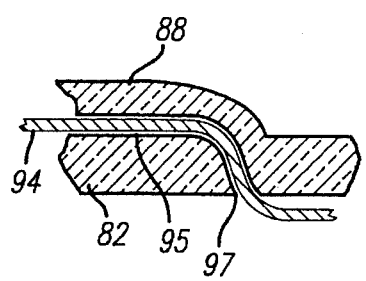
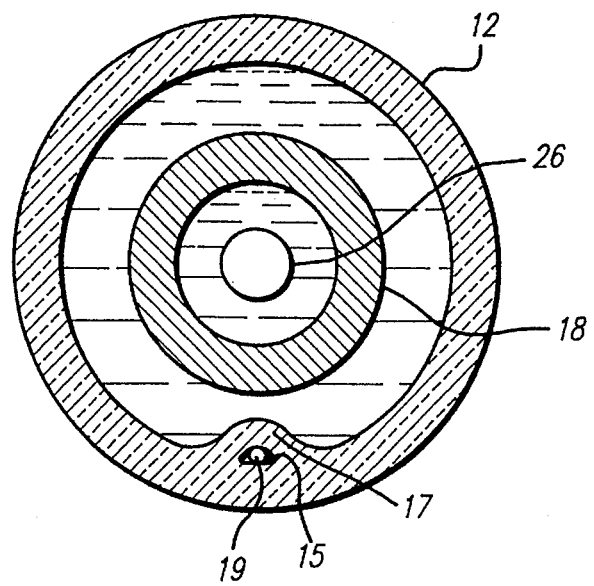
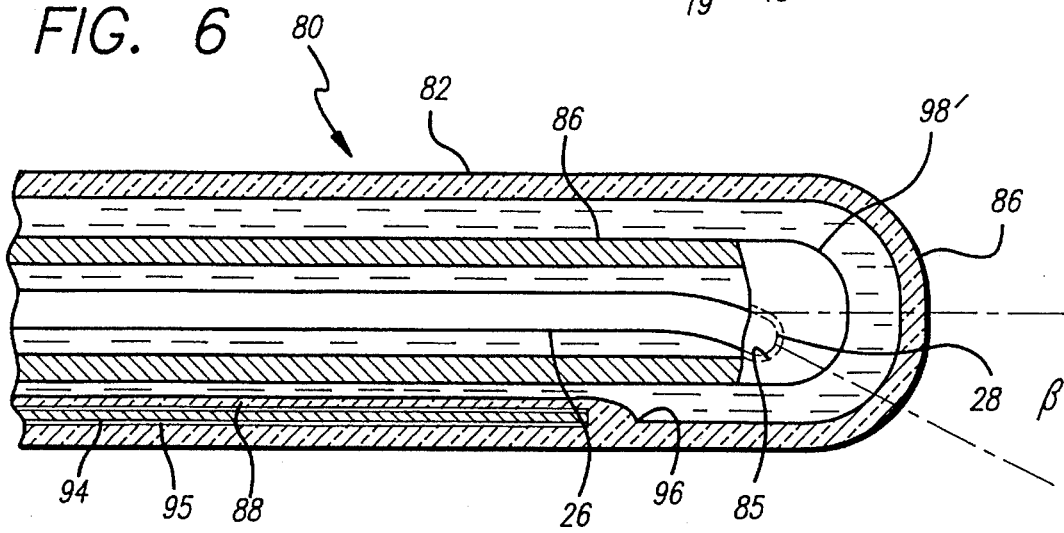

ULTRASOUND DIAGNOSTIC PROBE HAVING NON-ROTATING ACOUSTIC IMAGING WAVEGUIDE

RELATED APPLICATION

This invention relates to application Ser. No. 08/373,682 filed on Jan. 17, 1995, and owned by the assignee of this application.

BACKGROUND OF THE INVENTION

1. Field of the Invention

This invention relates to catheter systems for intravascular ultrasonic imaging, and more particularly, to a catheter having a non-rotating acoustic imaging waveguide that permits an ultrasonic beam to be rotated continuously through an area of interest within a vascular vessel.

2. Description of Related Art

Ultrasonic imaging systems are increasingly desirable for use in catheter-based probes to produce high definition images of internal surface characteristics of a blood vessel of a human body. Catheter-based probes typically comprise a flexible tubular element that is adapted to be inserted into a blood vessel in the vascular system. For example, such a probe may be inserted into the femoral artery of a patient in order to examine the coronary vessels and identify any stenosis or occlusion present within the vessels. This procedure can avoid the need for more invasive diagnostic techniques which might increase the risk to the patient and the associated recovery time. Catheter-based ultrasonic imaging is also known to improve the effectiveness of interventional therapies, such as angioplasty, atherectomy, laser ablation, and drug delivery, by enabling such therapies to be specifically directed where they will be most effective, and to evaluate the outcome of such therapy.

The ultrasonic imaging systems of these catheters typically comprise a piezoelectric transducer that generates an ultrasonic signal in response to an external electrical excitation. The ultrasonic signal is directed to an area of interest within a vessel, where it propagates through the blood until it reaches the interior surface of the vessel. Reflections of the signal, or echoes, return to the piezoelectric transducer, which converts these echoes to corresponding electrical signals. The electrical signals are then collected, processed and displayed as a two-dimensional image on a CRT screen.

In order to obtain a complete image of the interior surface area of the vessel, it is necessary to sweep the ultrasonic signal in a pattern about an axis of the vessel. Various techniques have been proposed to sweep the ultrasonic signal in the desired pattern which include the placement of the piezoelectric transducer in the distal end of the catheter. The transducer may be rotated directly to sweep the ultrasonic signal in the desired pattern, or the transducer may be fixed within the catheter and a reflective surface rotated to sweep the ultrasonic signal in the desired pattern. See U.S. Pat. No. 5,000,185, issued to Yock, for METHOD FOR INTRAVASCULAR TWO-DIMENSIONAL ULTRASONOGRAPHY AND RECANALIZATION. In this reference, torque for the rotation is provided by an external motor connected through the catheter by a torque cable to either the transducer or the reflective surface. Alternatively, a fluid coupled turbine may be disposed in the distal end of the catheter to provide the rotational torque. See U.S. Pat. No. 5,271,402, issued to Yeung et al., for TURBINE DRIVE MECHANISM FOR STEERING ULTRASOUND SIGNALS. In yet another alternative technique, a micro-motor may be disposed in the distal end of the catheter to provide the rotational torque. See U.S. Pat. No. 5,176,141, issued to Bom et al., for DISPOSABLE INTRA-LUMINAL ULTRASONIC INSTRUMENT.

There are numerous disadvantages associated with placing the piezoelectric transducer in the distal end of the catheter. The transducer may emit leakage currents inside the patient that can induce fibrillation when the probe images a coronary artery. Electrical wires that connect the transducer to external circuitry inherently act as antennas and receive radio frequency (RF) interference present within the environment of the catheterization laboratory. This RF interference may appear as noise in the electrical signals travelling to and from the transducer which distorts the two-dimensional image.

Another disadvantage of placing the transducer at the distal end of the catheter is that it increases the difficulty of varying the frequency of the ultrasonic signal. The piezoelectric transducer has a frequency of operation determined by its thickness. It may be desirable for the probe operator to adjust the transducer frequency in order to obtain a more precise image resolution or to illuminate a particular range of interest within the vessel. The transducer thickness is limited by the rather confined space within the distal end of the catheter, and the transducer cannot be easily replaced during catheterization.

Yet another disadvantage of placing the transducer at the distal end of the catheter is its associated expense. The catheter is typically discarded after a single use in order to prevent the transmission of disease. The transducer is costly to manufacture and its disposal increases the already high cost of probe-catheterization techniques. Moreover, the higher resolution transducers are among the most expensive to manufacture, which tends to discourage use of such transducers in favor of less desirable imaging systems.

An alternative approach to these prior art techniques is to dispose the piezoelectric transducer external to the patient, and to direct the ultrasonic signal into the catheter by use of an acoustic waveguide. To sweep the ultrasonic signal in the desired pattern, the entire acoustic waveguide is rotated by an external device, such as a motor. See U.S. Pat. No. 5,284,148, issued to Dias et al. for INTRACAVITY ULTRASOUND DIAGNOSTIC PROBE USING FIBER ACOUSTIC WAVEGUIDES. This approach substantially minimizes the disposable elements of the catheter, and provides greater flexibility to the operator in terms of transducer selection. Nevertheless, rotation of the acoustic waveguide subjects the relatively delicate waveguide to undesirable mechanical stress which could potentially damage the waveguide or reduce its acoustic efficiency.

Accordingly, it would be desirable to provide a catheter-based ultrasonic imaging system capable of sweeping an ultrasonic signal in a pattern about an axis of the blood vessel, which overcomes the numerous disadvantages of the prior art.

SUMMARY OF THE INVENTION

In accordance with the teachings of this invention, a catheter apparatus for obtaining an image of interior characteristics of a vascular vessel is provided. The catheter apparatus comprises an outer tubular element adapted for insertion into the vascular vessel, a rotatable inner tubular element disposed within the outer tubular element, and a non-rotating acoustic waveguide disposed within the inner tubular element and coupled to a source of an ultrasonic signal located external to the vascular vessel. The inner tubular element is rotated about an axis of the vascular vessel by use of an external driving member, such as a motor. Sterile fluid disposed between the outer and inner tubular elements provides for acoustic coupling of the ultrasonic signal into the vessel, and further provides for lubrication of the rotating elements.

The inner tubular element is provided with an acoustic reflecting or refracting element that directs the ultrasonic signal from a distal end of the acoustic waveguide through the outer tubular element at an angle relative to the axis of the vascular vessel. In a first embodiment of the invention, the acoustic reflecting element comprises an acoustic reflective surface. The reflective surface directs the ultrasonic signal at an angle substantially transverse to the vessel axis. The reflective surface is disposed at a distal end of the inner tubular element, and rotates in cooperation with the inner tubular element. In a second embodiment of the invention, the acoustic refracting element comprises an acoustic refractive lens disposed at a distal end of the inner tubular element. The refractive lens directs the ultrasonic signal at an angle ranging from 10° to 85° relative to the axis of the vascular vessel.

A more complete understanding of the ultrasound diagnostic probe having a non-rotating acoustic imaging waveguide will be afforded to those skilled in the art, as well as a realization of additional advantages and objects thereof, by a consideration of the following detailed description of the preferred embodiment. Reference will be made to the appended sheets of drawings which will first be described briefly.

BRIEF DESCRIPTION OF THE DRAWINGS

FIG. 5 is a side sectional view of an intravascular ultrasound diagnostic probe using an acoustic waveguide and an acoustic refractive lens;

FIG. 6 is a side sectional view of an alternative embodiment of the ultrasound diagnostic probe of FIG. 5;

FIG. 7 is an end sectional view of the ultrasound diagnostic probe as taken through the section 7—7 of FIG. 1; and FIG. 8 is a partial side sectional view of the ultrasound diagnostic probe for use with a monorail guidewire.

DETAILED DESCRIPTION OF THE PREFERRED EMBODIMENT

This invention provides a catheter-based ultrasonic imaging system capable of sweeping an ultrasonic signal in a rotating pattern about an axis of a blood vessel. In general, the invention provides a catheter apparatus having a non-rotating acoustic waveguide and a rotating reflective or refractive element to direct an ultrasonic signal in a desired pattern within the blood vessel.

Figure 1:
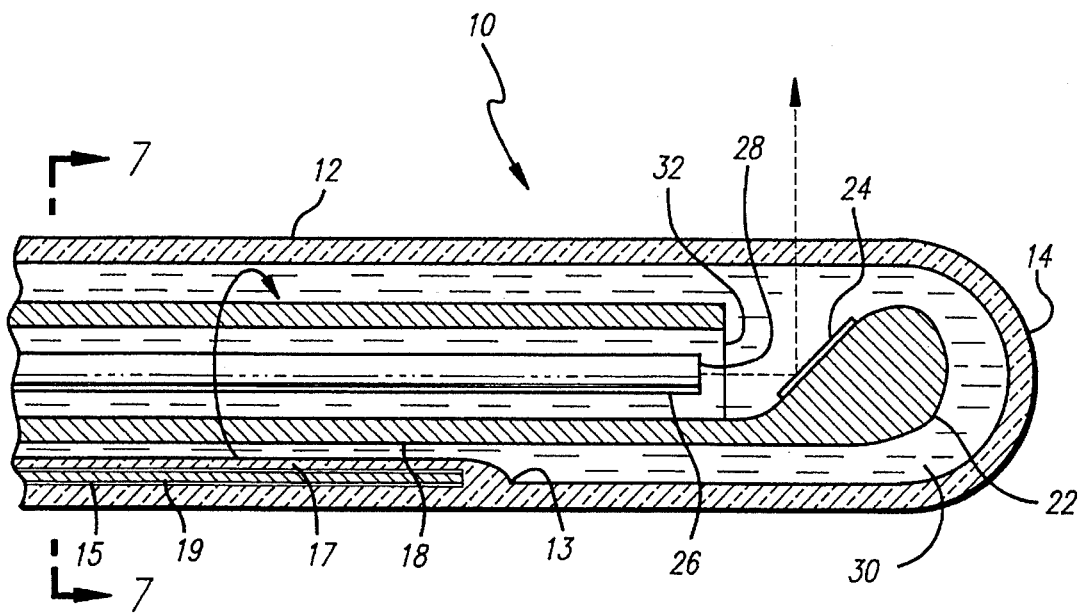
FIG. 1 is a side sectional view of the distal end of an intravascular ultrasound diagnostic probe using a non-rotating acoustic waveguide and an acoustic reflecting surface.

Referring first to FIG. 1, a distal end of a catheter 10 is illustrated. The catheter 10 is adapted for insertion into a blood vessel in the vascular system of a human body. The catheter 10 comprises an elongated outer tubular element 12 having a generally rounded tip 14. The outer tubular element 12 may be formed as a single extrusion of a flexible plastic material, such as polystyrene, polypropylene or other type of plastic. The outer tubular element 12 necessarily provides a smooth surface that can be readily inserted into the blood vessel without undesired friction. It is further desirable that the outer tubular element 12 be comprised a substantially acoustically transparent material to allow an ultrasonic signal to be transmitted therethrough. Alternatively, a substantially transparent window can be provided in the region of the distal end of the catheter 10.

An inner tubular element 18 is disposed coaxially within the outer tubular element 12. The inner tubular element 18 may be formed of a torsionally stiff material, such as coiled metal wire of one or more layers. Unlike the outer tubular element 12, however, the inner tubular element 18 does not come in contact with the patient. Accordingly, the smoothness of the inner tubular element 18 is less critical than its ability to withstand a rotational torque, for reasons that will be fully understandable from the description which follows. The inner tubular element 18 further includes an opening 32 disposed just prior to a rounded distal end 22 thereof. The distal end 22 is formed to a greater thickness than the relatively thin walls of the tubular element, such that a bulb-like end for the inner tubular element 18 is provided. The distal end 22 has an angular portion which supports a reflective surface 24. The reflective surface 24 may be comprised of a thin coating of acoustic reflective material deposited on the angular portion of the distal end 22 of the inner tubular element 18. Preferably, the angle of the reflective surface 24 is approximately 45° with respect to the axis of the inner tubular element 18, though it should be apparent that alternative angles can be selected.

An acoustic waveguide 26 is disposed coaxially within the inner tubular element 18 and which extends the length of the catheter 10. The acoustic waveguide 26 has a distal end 28 that is disposed approximately adjacent to, or just prior to, the opening 32 of the inner tubular element 18. As known in the art, an acoustic waveguide is similar to an optical waveguide, i.e., optical fiber. Both acoustic waveguides and optical waveguides typically comprise a central core and an outer cladding which surrounds the core and is in intimate acoustic contact with the core. The purpose of the cladding is to keep the acoustic signals within the core. Ideally, the waveguide guides the acoustic signals which reflect off the cladding and remain within the core. It is anticipated that the acoustic waveguide 26 be comprised of a glass material having generally high flexibility.

Figure 2:
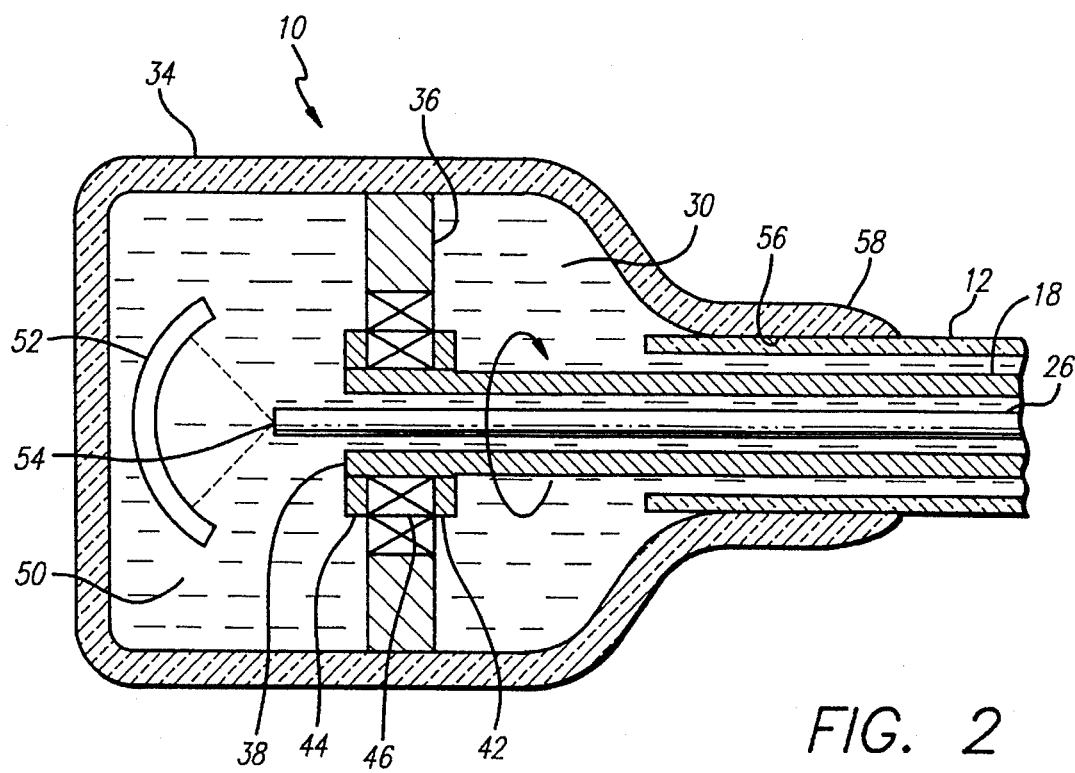
FIG. 2 is a side sectional view of the proximal end of the ultrasound diagnostic probe of FIG. 1.

Referring now to FIG. 2, a proximal end of a catheter 10 is illustrated. The proximal end comprises a housing 34 having a neck portion 58 that is adapted to receive the proximal end of the outer tubular element 12 inserted therein. An inner surface 56 of the neck portion 58 provides a bonding region between the housing 34 and the outer tubular element 12. A motor is disposed within the housing 34, comprising a stator portion 36, rotor portions 42, 44, and inductive coil 46. A proximal end portion 38 of the inner tubular element 18 couples axially with the rotor portions 42, 44. Accordingly, rotation of the rotor portions 42, 44 of the motor with respect to the stator portion 36 causes likewise rotation of the inner tubular element 18. As known in the art, a rotational rate of the inner tubular element 18 can be controlled through electrical control of the motor. It is anticipated that the motor operate at a rotational rate ranging from 100 to 20,000 rpm, with a preferred rotational rate of approximately 1,600 rpm.

A piezoelectric transducer 52 is also disposed within a chamber 50 of the housing 34. The piezoelectric transducer 52 is spherically shaped having convex and concave surfaces, and is comprised of a crystalline material that is machined to a desired thickness and radius of curvature. As known in the art, the thickness of the transducer 52 governs the frequency of an output acoustic signal of the transducer, and a radius of curvature of the transducer governs its focal point. The convex and concave surfaces of the piezoelectric transducer 52 may be further metallized with chromium and/or gold electrode films so as to improve the acoustic generating capability of the transducer. The proximal end 54 of the acoustic waveguide 26 is located at the focal point of the transducer 52. Electrical signals drive the piezoelectric transducer 52 so that it generates emitted acoustic signals that have a frequency in the ultrasonic range between 10 MHz and 50 MHz.

The catheter 10 further comprises an acoustical coupling fluid 30 contained within the outer tubular element 12 and the housing 34. The fluid 30 fills the spaces between the outer tubular element 12 and the inner tubular element 18, and between the inner tubular element 18 and the acoustic waveguide 26. The fluid 30 inside the chamber 50 of the housing 34 couples acoustic signals produced by the transducer 52 into the acoustic waveguide 26. Similarly, the fluid at the distal end of the catheter 10 couples acoustic signals between the acoustic waveguide, the reflective surface 24 and the outer tubular element 12. It is anticipated that acoustic impedance matching layers on the transducer 52 and on both ends of the acoustic waveguide 26 will provide efficient conduction of acoustic signals between both the transducer and the proximal end of the waveguide as well as between the distal end of the waveguide and the distal coupling fluid 30. At the same time, the fluid 30 acts as a lubricant between the rotating inner tubular element 18 and the non-rotating outer tubular element 12 and acoustic waveguide 26.

In operation, the distal end of the catheter 10 is inserted into a vascular vessel of the patient, such as the femoral artery. The inner tubular element 18 and acoustic waveguide 26 of the catheter 10 may not yet be inserted into the outer tubular element 12. Instead, the outer tubular element 12 may contain a guidewire that enables an operator of the catheter to steer the distal end of the catheter to a desired location, such as adjacent a coronary artery. The guidewire may further enable the operator to monitor the progress of the catheter as it travels through the vascular vessel by use of external imaging techniques, such as fluoroscopy. Once the desired location is reached, the operator may remove the guidewire and insert the inner tubular element 18 and acoustic waveguide 26 in its place within the outer tubular element 12.

To provide for this guidewire, the outer tubular element 12 of FIG. 1 may additionally comprise a lumen 15 causing an inner surface of the outer tubular element to include an inwardly facing dimple 17, as further illustrated in FIG. 7. The lumen 15 may carry a guidewire 19 that extends the majority of the length of the catheter 10 to a point 13 prior to the distal end of the outer tubular element 12. The guidewire 19 does not extend all the way to the distal end of the outer tubular element 12, otherwise the guidewire may interfere with ultrasonic imaging operations.

Figure 4:
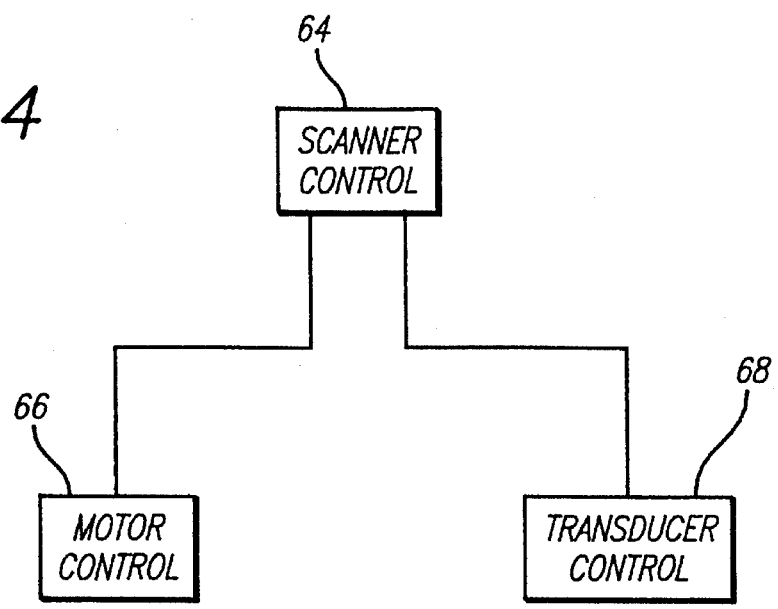
FIG. 4 is a block diagram illustrating a control structure for the ultrasound diagnostic probe.

An ultrasonic imaging operation utilizing the catheter 10 is described with reference to the block diagram of FIG. 4. The operator provides instructions to a scanner control device 64, which in turn directs operation of a motor control device 66 and a transducer control device 68. The motor control device 66 provides control signals and electrical current to the motor within the housing 34 to cause the inner tubular element 18 to rotate at a desired rate. The transducer control device 68 provides control signals and electrical excitation to the piezoelectric transducer 52 to cause the transducer to produce acoustic signals that are coupled into the acoustic waveguide 26 at its proximal end 54.

The acoustic signals are emitted from the acoustic waveguide 26 at its distal end 28 and reflected off the reflective surface 24 to pass through the outer tubular element 12. The 45° angle of the reflective surface 24 with respect to the axis of the acoustic waveguide 26 causes the acoustic signals emitted from the waveguide to be reflected at an angle substantially transverse to the axis, or 90° with respect to the axis. The acoustic signals then travel through the body fluid within the vascular vessel until they encounter a change in acoustic impedance, which occurs when the emitted acoustic signals strike body tissue. The reflected acoustic signals then travel back following the same path to the transducer 52. The transducer 52 converts the reflected acoustic signals into corresponding electrical signals that contains information on the contours of the inside surface of the vessel. The high frequency of the acoustic signal relative to the rotation rate of the reflective surface 24 insures that image data for each angular position along the interior surface of the vessel can be obtained. The signals representing each angular position are collected, processed and displayed on a CRT screen as a two-dimensional, cross-sectional image.

Figure 3:
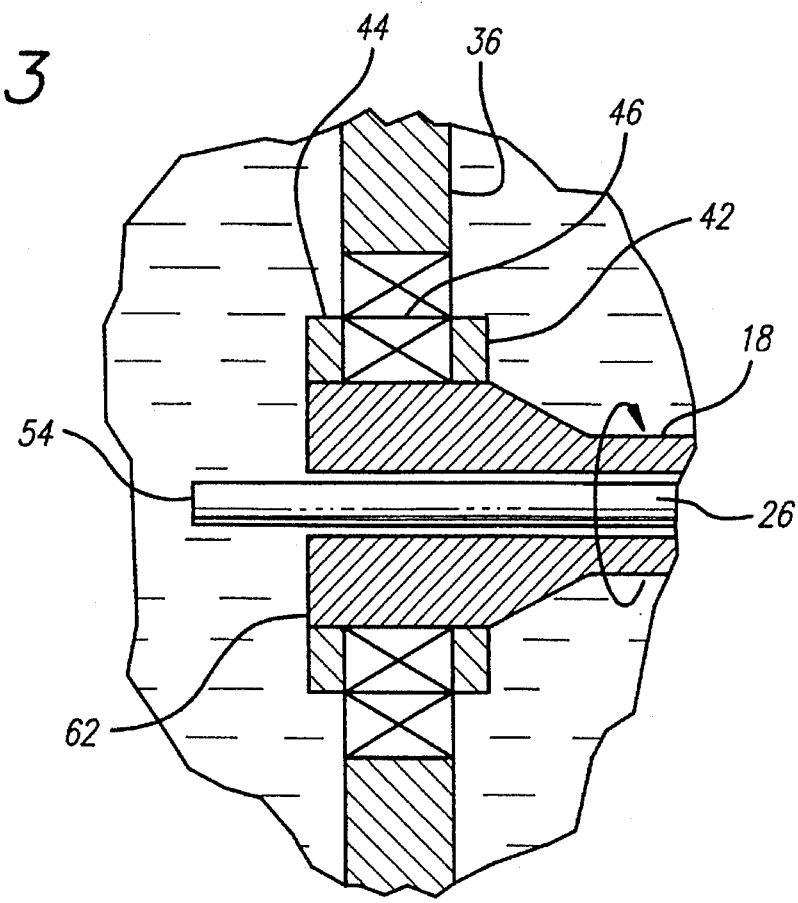
FIG. 3 is an enlarged side sectional view of an alternative embodiment of the proximal end of the ultrasound diagnostic probe of FIG. 1.

FIG. 3 illustrates an alternative embodiment of the proximal end of the catheter 10. The proximal end of the inner tubular element 18 flares outwardly to a wide portion 62 at the coupling point with the rotors 42, 44. The wide portion 62 is capable of withstanding a greater amount of stress due to the rotational torque of the motor, over that of the uniform width inner tubular element 18 of FIG. 2. In addition, it is anticipated that the inner tubular element 18 be discarded along with the outer tubular element 12 upon completion of a single use of the catheter 10. The wide portion 62 enables easier attachment between the inner tubular element 18 and the motor. The remaining elements illustrated in FIG. 3 are as described above with respect to FIG. 2.

Referring now to FIGS. 5 and 7, an alternative embodiment of the distal end of a catheter 80 is illustrated. In this embodiment, the catheter 80 is adapted for ultrasonic imaging while it is traveling through the blood vessel, as opposed to imaging at a fixed axial location. As in FIG. 1, the catheter 80 comprises an elongated outer tubular element 82 having a generally rounded tip 14. The outer tubular element 82 is similar to the outer tubular element 12 of FIG. 1, and may also be formed as a single extrusion of a flexible plastic material, such as polystyrene, polypropylene or other type of plastic. As in the outer tubular element 12 of FIG. 1, the outer tubular element 82 of FIGS. 5 and 6 may comprise a lumen 95 causing an inner surface of the outer tubular element to include an inwardly facing dimple 88. The lumen 95 carries a guidewire 94 that extends the majority of the length of the catheter 80 to a point 96 prior to the distal end of the outer tubular element 82. The guidewire 94 does not extend all the way to the distal end of the outer tubular element 82, otherwise the guidewire may interfere with ultrasonic imaging operations. The lumen 95 and guidewire 94 are substantially the same as the lumen 15 and guidewire 19, respectively, that are described above with respect to FIGS. 1 and 7.

An inner tubular element 86 is disposed coaxially within the outer tubular element 82. As with the inner tubular element 18 of FIG. 1, the inner tubular element 86 may be formed of a torsionally stiff material, such as one or more layers of coiled metal wire. The inner tubular element 86 further includes a lens 98 disposed at a distal end thereof. The lens 98 is formed to a greater thickness than the relatively thin walls of the inner tubular element 86, and may alternatively be comprised of a different acoustic material that is formed to the inner tubular element.

An acoustic waveguide 26 is disposed coaxially within the inner tubular element 86 and which extends the length of the catheter 80. The acoustic waveguide 26 has a distal end 28 that extends into a pocket 85 formed in a back surface of the lens 98. The pocket 85 may be disposed at an angle α with respect to the central axis of the catheter 80, and the acoustic waveguide 26 would bend at the distal end 28 in order to couple with the pocket 85. It is anticipated that the angle α be in a range between approximately 10° and 30°.

In operation, the distal end of the catheter 80 is inserted into a vascular vessel of the patient, such as the femoral artery. The inner tubular element 86 and acoustic waveguide 26 will be already inserted into the outer tubular element 82, unlike the embodiment of FIGS. 1–3. The guidewire 94 enables the operator of the catheter 80 to steer the distal end of the catheter as it travels through the vessel. At the same time, the catheter 80 may be used to conduct ultrasonic imaging of the vessel. The operator will activate the motor to commence rotation of the inner tubular element 86, and the transducer to conduct ultrasonic signals through the waveguide 26 to the refractive lens 98. As the refractive lens 98 rotates in cooperation with the inner tubular element 86, the distal end 28 of the non-rotating acoustic waveguide 26 bends in a rotating manner to maintain coupling with the pocket 85. The refractive lens 98 further bends the ultrasonic signals so that they are transmitted outwardly from the distal end 86 of the outer tubular element 82. The rotation of the inner tubular element 86 produces a cone-shaped projection of half angle α of acoustic energy directed forward into the vessel, providing the operator with a forward looking image into the vessel as the catheter 80 is manipulated into the vessel.

FIG. 6 illustrates another alternative embodiment of the distal end of catheter 80. The elements of the catheter 80 are identical to that described above, with the exception of the refractive lens 98' that is modified to provide a half angle β. The angle β is greater than the angle α due either to the material properties of the refractive lens 98', the angle of the pocket 85, or a combination of both. It is anticipated that the angle β be in a range between approximately 30° and 85°.

Referring finally to FIG. 8, an alternative embodiment of the outer tubular element 82 of the catheter 80 is illustrated. As in FIGS. 5 and 6, a lumen 95 is provided to carry a guidewire 94. Instead of terminating the guidewire 94 at the point 96, a port 97 is provided enabling the guidewire to exit the lumen 95. In operation, the guidewire 94 may be initially threaded into the vessel. The exposed proximal end of the guidewire 94 external to the patient may then be inserted into the port 97, and through the lumen 95. As a result, the catheter 80 may then slide along the pre-inserted guidewire within the vessel. The acoustic waveguide 26 may be carrying acoustic signals to image the vessel as the catheter is being inserted. This type of guidewire system is referred to as a monorail guidewire. It should be apparent that the monorail guidewire of FIG. 8 can also be advantageously utilized in the catheter 10 of FIGS. 1 and 2.

Having thus described a preferred embodiment of the ultrasound diagnostic prove having a non-rotating acoustic imaging waveguide, it should be apparent to those skilled in the art that certain advantages of the within system have been achieved. It should also be appreciated that various modifications, adaptations, and alternative embodiments thereof may be made within the scope and spirit of the present invention. The invention is further defined by the following claims.

What is claimed is:

1. A catheter apparatus for obtaining an image of a vascular vessel comprising:

an outer tubular element;

an inner tubular element disposed coaxially within said outer tubular element and means for rotating said inner tubular element about an axis of said vascular vessel;

a non-rotating acoustic waveguide disposed within said inner tubular element coupled to an acoustic transducer located external to the vascular vessel; and means for directing said ultrasonic signal from a distal end of said acoustic waveguide through said outer tubular element.

2. The catheter apparatus of claim 1, wherein said directing means further comprises an acoustic reflective surface.

3. The catheter apparatus of claim 2, wherein said reflective surface is disposed at a distal end of said inner tubular element.

4. The catheter apparatus of claim 1, wherein said directing means further comprises an acoustic lens disposed at a distal end of said inner tubular element.

5. A catheter apparatus for obtaining an image of a vascular vessel comprising:

an outer tubular element adapted for insertion into the vascular vessel;

a rotatable inner tubular element disposed within said outer tubular element and means for rotating said inner tubular element about an axis of said vascular vessel;

a non-rotating acoustic waveguide disposed within said inner tubular element coupled to a source of an ultrasonic signal located external to the vascular vessel; and means associated with said inner tubular element for directing said ultrasonic signal from a distal end of said acoustic waveguide through said outer tubular element at an angle relative to said axis of said vascular vessel.

6. The catheter apparatus of claim 5, wherein said directing means further comprises an acoustic reflective surface and said angle is substantially transverse to said axis.

7. The catheter apparatus of claim 6, wherein said reflective surface is disposed at a distal end of said inner tubular element.

8. The catheter apparatus of claim 5, wherein said directing means further comprises an acoustic lens disposed at a distal end of said inner tubular element.

9. The catheter apparatus of claim 8, wherein said acoustic lens further comprises means for coupling with said non-rotating acoustic waveguide.

10. The catheter apparatus of claim 8, wherein said angle is from 10° to 85° relative to the axis of the vascular vessel.

11. The catheter apparatus of claim 5, wherein said rotating means is located external to said vascular vessel.

12. The catheter apparatus of claim 5, further comprising a sterile coupling fluid disposed between said outer tubular element and said inner tubular element, and between said inner tubular element and said acoustic waveguide.

13. The catheter apparatus of claim 5, further comprising a lumen provided in an inner portion of said outer tubular element capable of carrying a flexible guidewire.

14. The catheter apparatus of claim 13, further comprising a port disposed in said outer tubular element and coupled to said lumen, said port capable of carrying a monorail guidewire.

15. The catheter apparatus of claim 5, further comprising means for coupling said inner tubular element to said rotating means.

16. A method for imaging an interior surface of a vascular vessel comprising the steps of:

generating an ultrasonic signal using a transducer located external to the vascular vessel;

directing the ultrasonic signal into the vascular vessel through a non-rotating waveguide disposed within a catheter inserted into the vascular vessel;

sweeping the signal continuously in a predetermined pattern about the interior surface of the vascular vessel by rotating an acoustic guiding member within the catheter;

receiving the signal after reflection from the interior surface of the vascular vessel; and producing an image from the reflected signal.

17. The method as in claim 16, wherein the ultrasonic signal is directed through the non-rotating waveguide in a direction generally axial relative to the vascular vessel and is directed by said acoustic guiding member in a substantially transverse direction.

18. The method as in claim 17, wherein said acoustic guiding member comprises a reflective surface.

19. The method as in claim 16, wherein the ultrasonic signal is directed through the non-rotating waveguide in a direction generally axial relative to the vascular vessel and is directed at a forward angle from 10° to 85° relative to the axis of the vascular vessel.

20. The method as in claim 19, wherein said acoustic guiding member comprises a lens.

* * * * *